US010123766B2

(12) United States Patent
Mourad et al.

(10) Patent No.: US 10,123,766 B2
(45) Date of Patent: Nov. 13, 2018

(54) ULTRASOUND STYLET

(71) Applicant: University of Washington through its Center for Commercialization, Seattle, WA (US)

(72) Inventors: Pierre D. Mourad, Seattle, WA (US); Samuel R. Browd, Seattle, WA (US); Brian MacConaghy, Kent, WA (US); Revathi Murthy, Herndon, VA (US); Nathaniel Coulson, Liberty Lake, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 873 days.

(21) Appl. No.: 14/359,075

(22) PCT Filed: Dec. 10, 2012

(86) PCT No.: PCT/US2012/068802
§ 371 (c)(1),
(2) Date: May 16, 2014

(87) PCT Pub. No.: WO2013/086521
PCT Pub. Date: Jun. 13, 2013

(65) Prior Publication Data
US 2014/0323857 A1 Oct. 30, 2014

Related U.S. Application Data

(60) Provisional application No. 61/568,490, filed on Dec. 8, 2011, provisional application No. 61/620,335, filed
(Continued)

(51) Int. Cl.
*A61B 8/08* (2006.01)
*A61B 8/12* (2006.01)
(Continued)

(52) U.S. Cl.
CPC .......... *A61B 8/0841* (2013.01); *A61B 8/0808* (2013.01); *A61B 8/0858* (2013.01);
(Continued)

(58) Field of Classification Search
CPC ......... A61B 8/12; A61B 8/0841; A61B 8/445; A61B 8/462; A61B 8/5207;
(Continued)

(56) References Cited

U.S. PATENT DOCUMENTS

| 4,887,606 A | 12/1989 | Yock |
| 5,638,819 A * | 6/1997 | Manwaring .......... A61B 1/0005 600/103 |

(Continued)

FOREIGN PATENT DOCUMENTS

| CN | 1886095 A | 12/2006 |
| CN | 101208045 A | 6/2008 |

(Continued)

OTHER PUBLICATIONS

Extended European Search Report dated Jun. 23, 2015, issued in corresponding European Application No. 12 85 5365.8, filed Dec. 10, 2012, 6 pages.
(Continued)

*Primary Examiner* — Bo J Peng
(74) *Attorney, Agent, or Firm* — Christensen O'Connor Johnson Kindness, PLLC; Ryan Dodge

(57) ABSTRACT

A stylet (100) includes a handle assembly (102) with an indicator display (112) and a stiff wire assembly (120) extending distally from the handle assembly (102) having a non-imaging ultrasonic device on a distal end. The stylet includes a circuit assembly having one or more of a pulser (120), a transmit/receive chip (132), a bandpass filter (134), a differential amplifier (136), an ADC (138), and an MCU (140), operable to control the operation of the ultrasonic
(Continued)

device and to receive and analyze data from the ultrasonic device to facilitate implantation of a device such as a catheter.

23 Claims, 7 Drawing Sheets

Related U.S. Application Data on Apr. 4, 2012, provisional application No. 61/667,535, filed on Jul. 3, 2012.

(51) Int. Cl.
*A61B 8/00* (2006.01)
*A61B 17/00* (2006.01)
*A61B 17/34* (2006.01)
*A61M 25/09* (2006.01)
*A61B 90/11* (2016.01)

(52) U.S. Cl.
CPC .............. *A61B 8/12* (2013.01); *A61B 8/445* (2013.01); *A61B 8/4494* (2013.01); *A61B 8/462* (2013.01); *A61B 8/488* (2013.01); *A61B 8/5207* (2013.01); *A61B 8/54* (2013.01); *A61B 8/56* (2013.01); *A61B 17/00234* (2013.01); *A61B 17/3421* (2013.01); *A61B 17/3468* (2013.01); *A61B 17/3478* (2013.01); *A61M 25/09* (2013.01); *A61B 8/4483* (2013.01); *A61B 8/461* (2013.01); *A61B 90/11* (2016.02)

(58) Field of Classification Search
CPC . A61B 17/3421; A61B 17/00234; A61B 8/56; A61B 8/54; A61B 8/488; A61B 8/4494; A61B 8/0858; A61B 17/3478; A61B 17/3468; A61B 8/0808; A61B 90/11; A61B 8/4483; A61B 8/46; A61M 25/09
See application file for complete search history.

(56) References Cited

U.S. PATENT DOCUMENTS

| | | | |
|---|---|---|---|
| 5,690,117 A * | 11/1997 | Gilbert | ..................... A61B 1/05 600/342 |
| 5,860,951 A | 1/1999 | Eggers | |
| 6,272,370 B1 | 8/2001 | Gillies | |
| 6,709,427 B1 | 3/2004 | Nash | |
| 7,766,839 B2 | 8/2010 | Rogers | |
| 2002/0128639 A1* | 9/2002 | Pless | ................... A61B 17/2202 606/27 |
| 2003/0181807 A1 | 9/2003 | Murphy | |
| 2005/0033177 A1 | 2/2005 | Rogers | |
| 2005/0049510 A1 | 3/2005 | Haldeman | |
| 2005/0288618 A1 | 12/2005 | Jenson | |
| 2006/0106315 A1 | 5/2006 | Edens | |
| 2006/0224142 A1 | 10/2006 | Wilson | |
| 2007/0129628 A1* | 6/2007 | Hirsh | ....................... A61B 8/12 600/411 |
| 2008/0091104 A1 | 4/2008 | Abraham | |
| 2008/0114309 A1* | 5/2008 | Zuckerman | ........ A61B 17/3403 604/264 |
| 2008/0319376 A1 | 12/2008 | Wilcox | |
| 2009/0005675 A1 | 1/2009 | Grunwald | |
| 2011/0106052 A1 | 5/2011 | Chiang | |
| 2011/0313282 A1 | 12/2011 | Frankel | |
| 2011/0313328 A1 | 12/2011 | Nita | |
| 2011/0319927 A1 | 12/2011 | Nita | |
| 2012/0059285 A1 | 3/2012 | Soltani | |
| 2012/0078140 A1 | 3/2012 | Nita | |
| 2012/0143029 A1 | 6/2012 | Silverstein | |

FOREIGN PATENT DOCUMENTS

| | | |
|---|---|---|
| CN | 101854853 A | 10/2010 |
| GB | 1 298 707 A | 12/1972 |
| JP | 59-172406 U1 | 11/1984 |
| JP | 3-16946 U | 2/1991 |
| JP | 05-056912 B2 | 3/1993 |
| JP | 2010/532227 A | 7/2010 |
| WO | WO 2011/085401 A1 | 7/2011 |

OTHER PUBLICATIONS

Chinese Notification of First Office Action dated Aug. 27, 2015, issued in corresponding Chinese Application No. 201280060520.0, filed Dec. 10, 2012, 26 pages.
Japanese Office Action dated Sep. 6, 2016, issued in corresponding Japanese Application No. 2014-546177, filed Dec. 10, 2012, 20 pages.
International Search Report dated Apr. 30, 2013, issued in corresponding International Application No. PCT/US2012/068802, filed Dec. 10, 2012, 3 pages.

* cited by examiner

ULTRASOUND STYLET

STATEMENT OF GOVERNMENT LICENSE RIGHTS

This invention was made with government support under W81XWH-11-2-0109 awarded by the U.S. Army Medical Research & Material Command. The government has certain rights in the invention.

BACKGROUND

Elongate tubular members or devices such as needles, stents, catheters, etc., are used extensively in modern medicine for a variety of purposes. For example, such elongate devices are used for medicant delivery, biopsy, mechanical treatment of tissues, removal or relief of occlusions, pressure reduction, and the like. Usually precise positioning of the device is critical to achieve the desired result. However, accurately targeting and intersecting a particular internal location in a three-dimensional body is a challenging endeavor.

Placement of the device is frequently performed manually. The physician relies on external landmarks, knowledge of anatomy, experience, and skill to accurately place the device. More recently, developments in medical imaging technologies, such as computed tomography imaging, magnetic resonance imaging, and ultrasound imaging, have provided some capability for image-guided placement of catheters in particular body locations. In rare instances real-time medical imaging may be available during placement of the catheter. In other instances a previously obtained image may be available as a guide for catheter placement.

Although image-guided catheter placement is efficacious, medical imaging systems are typically not readily available, especially during emergent procedures. Modern medical imaging devices are expensive to purchase and to operate, are time consuming to set up, and usually are fixed or, at best, only semi-portable. These imaging systems typically require considerable training and specialized skills to operate. In particular, these imaging systems are frequently not available in intensive care units, emergency rooms, or pre-hospital settings.

Even if a real-time imaging system is available, however, the imaging system requires the surgeon to orient the stylet while looking at a monitor rather than looking at the stylet itself, further complicating accurate placement of the device. In addition, some such systems require two individuals to perform the combined imaging/catheter-insertion procedure when used simultaneously, simply because two hands are generally required to guide the catheter, and at a minimum one hand is required to run the real-time imaging system.

An example of a medical procedure that would benefit from improvements in the accurate placement of a catheter is ventriculosotomy, or the placement of an external ventricular drain (EVD). In the human brain the ventricular system includes a set of ventricles or interior volumes that produce and contain cerebrospinal fluid (CSF). The ventricles are interconnected with small flow paths (e.g., foramina), and the system is fluidly connected with the central canal of the spinal cord. The CSF flows from the lateral ventricles, through the third and fourth ventricles, and into the central canal of the spinal cord or the subarachnoid space. If the flow paths become blocked, for example, due to infection or the like, pressure within the ventricular system can rise, which can result in injury, for example, hydrocephalus.

An EVD is a catheter used in neurosurgery to relieve elevated intracranial pressure when the normal flow of CSF is obstructed. The EVD catheter is placed over a stiff guide wire or stylet that the surgeon uses to implant the catheter in the patient's brain. A small hole is cut through the skull, and the EVD catheter is inserted through the brain dura mater and into the interior of the brain until it enters the target ventricle.

Freehand placement of the EVD catheter requires the neurosurgeon to estimate the three-dimensional location of the target ventricle, usually based on external anatomical landmarks. The ventricle is typically only about 1 cm across, and may be located at a depth of 5 cm or more. Once the position of the target ventricle is estimated, the EVD catheter is urged through the brain toward the target ventricle. The freehand method does not provide any means to account for potential irregularities in the patient anatomy that are not apparent externally. Factors such as intracranial lesions, genetic variability, and the like, can also affect the location of the target ventricle.

Understandably, freehand placement of EVD catheters has a high failure rate, often requiring the physician to make multiple attempts, resulting in more than one pass through the brain tissue to accomplish the requisite placement of the EVD catheter. In a retrospective study, Toma et al. (2009, Neurosurgery 65:1197) demonstrated that 65% of catheter placements in the setting of inserting ventriculo-peritoneal shunts ended up outside of the target ventricle, with almost half of those requiring revision and reinsertion. Possible complications associated with misplacement of an EVD catheter can include intra-cerebral hemorrhage, stroke, damage to adjacent brain structures, as well as the need for re-operation to replace the malpositioned catheter. Higher infection rates are also reported when multiple EVD placement attempts are required.

Catheterization is a relatively common procedure and has applications in addition to EVD, including ventriculo-peritoneal shunt placement, central venous catheter placement, hemodialysis, epidural anesthesia, lumbar puncture, and the like.

There is a need for low-cost, easy to operate, and portable devices and methods for providing guidance to medical personnel to facilitate inserting elongate tubular members such as needles, stents, catheters, through tissue and into a body.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A stylet for use in medical procedures, for example to guide a catheter, needle, or other implement toward an internal location in a body, includes an indicator, and an elongate member having a non-imaging ultrasonic device fixed thereto. The non-imaging ultrasonic device is configured to generate ultrasonic waves in a direction aligned with the axis of the elongate member, and to receive scattered or reflected ultrasonic waves, that may be analyzed with an microprocessor to detect an internal feature, for example a tissue-fluid interface. The indicator is selectively activated to provide feedback to a surgeon that the stylet is in a desired alignment. In an embodiment, the indicator comprises a display that indicates a first status prompt when a desired alignment is detected, and a second status prompt when the desired alignment is not detected. The indicator may be visual, audio, and/or haptic, for example, and may be configured to provide feedback regarding a direction to pivot towards the desired alignment and/or a calculated distance to the internal feature.

In an embodiment the ultrasonic device has a single transducer configured to selectively operate in a transmit mode to generate ultrasonic pulses, and in a receive mode to detect scattered ultrasonic waves. In another embodiment, the ultrasonic device includes a plurality of ultrasonic transducers, for example, fewer than ten transducers that may be arranged in a coplanar array, and may be formed from a single crystal.

In an embodiment, the stylet further includes a pulser, a transmit/receive chip, a filter, and an analog-to-digital converter (ADC) mounted with the microprocessor to form a circuit assembly that is operable to analyze the detected ultrasonic waves. For example, the circuit assembly may be wirelessly connected to the ultrasonic device, or may be connected with a cable that extends through the elongate member.

In an embodiment, the stylet includes a handle enclosure that houses the indicator and circuit assembly, and the stylet further includes a power supply that is housed in the handle enclosure. The stylet may be fully disposable, partially disposable, or reusable.

In another embodiment, the stylet includes an external control unit that houses the microprocessor, pulser, transmit/receive chip, filter and ADC, and connects to the stylet ultrasonic device and indicator wirelessly or with a cable. The stylet portion of the system may be disposable, and the external control unit may be reusable.

In an embodiment, the stylet includes an elongate catheter that is configured to slidably receive the stylet elongate member, and may be, for example, a fish mouth catheter or a catheter with an acoustic lens in its distal end.

In an embodiment, the indicator is disposed directly over a proximal end of the elongate member, and is oriented perpendicular to the elongate member, such that a surgeon can view the indicator, elongate member and body directly while using the stylet.

A system for implanting a catheter or similar device includes a stylet, an ultrasonic device configured to be operated in amplitude (one dimensional) mode attached to a distal end of the stylet, an indicator attached to a proximal end of the stylet, and a circuit assembly having a microprocessor, pulser, transmit/receive chip, bandpass filter, and ADC. The circuit assembly is configured to control the ultrasonic device, to receive and analyze data from the ultrasonic device, and to control the status of the indicator. The ultrasonic device may be a single transducer, or an array of a plurality of transducers, which may be oriented in a coplanar arrangement, and may be formed from a single crystal. The indicator is configured to provide feedback to a user indicating a desired alignment of the stylet.

In an embodiment, the ultrasonic device is connected to the circuit assembly with a cable extending through the stylet. In another embodiment the ultrasonic device and circuit assembly are connected wirelessly.

In another embodiment the indicator is remote from the stylet and is connected to the stylet and ultrasonic device wirelessly or via a cable. The indicator may provide a visual prompt, an audible prompt, and/or a haptic prompt.

In an embodiment the system further comprises an elongate catheter that slidably receives the stylet, and that has an open distal end or a distal end that includes an acoustic window or lens. In an embodiment the indicator is disposed directly over the stylet. The system may be disposable, partially disposable, or reusable.

A method for guiding a stylet towards a target internal fluid-tissue boundary includes positioning a stylet, having a non-imaging ultrasonic device at its distal end and an indicator at its proximal end, on an outer surface of the tissue, activating the non-imaging ultrasonic device to transmit ultrasonic waves and detected scattered ultrasonic waves, receiving and analyzing the signals representing detected scattered ultrasonic waves, pivoting the stylet until the indicator provides a prompt indicating a desired alignment, and urging the stylet through the tissue toward the target. The indicator may provide a visual prompt, an audible prompt, and/or a haptic prompt.

In an embodiment the received signal is analyzed for one or more of timing and amplitude information, pulsatility information, and color Doppler information. The analysis may include determining if the received signal indicates amplitude, timing, depth, pulsatility, or blood-flow speed and/or direction characteristics that exceed predetermined thresholds.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
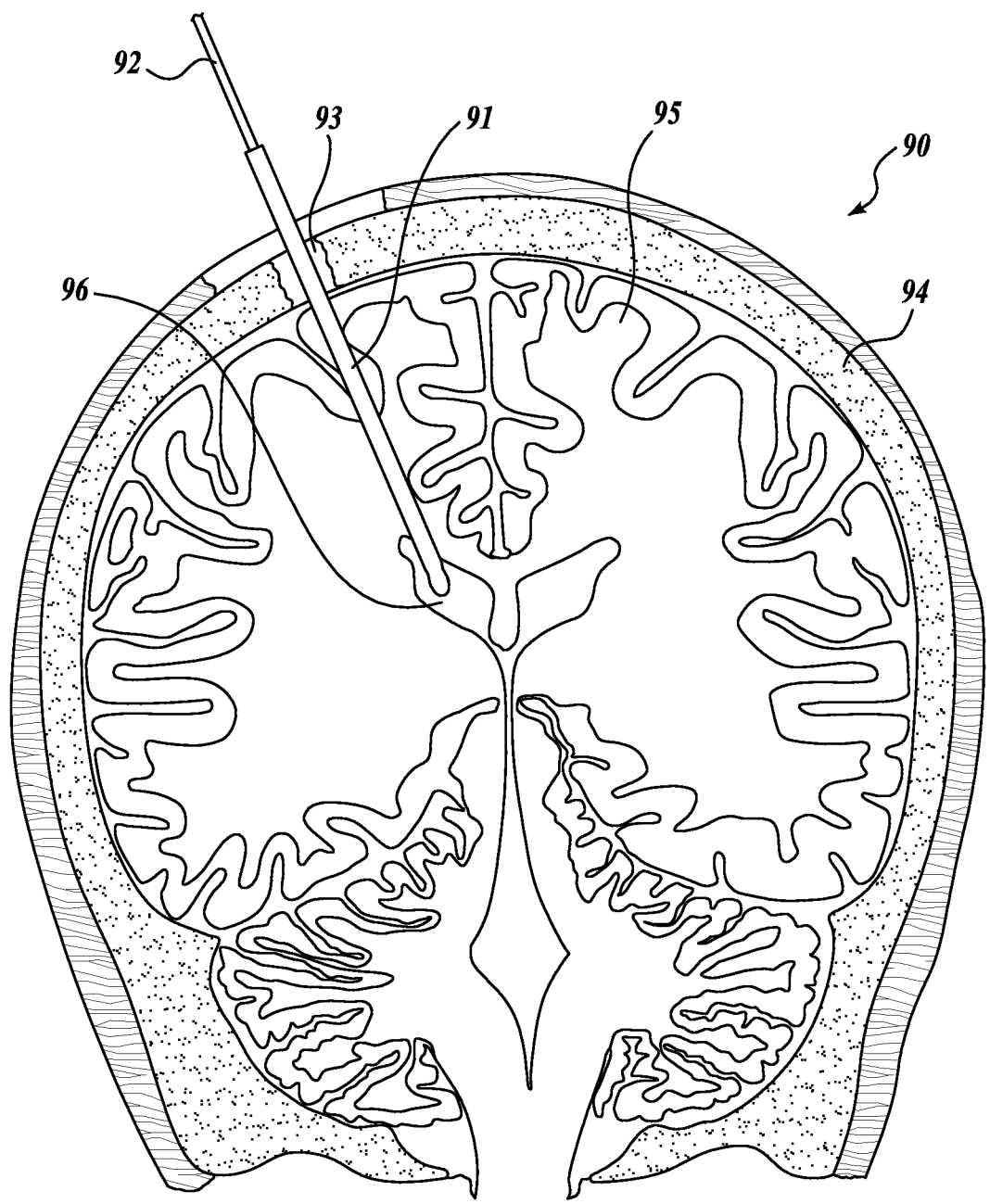
FIGS. 1A and 1B illustrate insertion of an external ventricular catheter using a prior art stiff wire stylet, FIG. 1A showing a desired placement of the catheter, and FIG. 1B showing an incorrect placement of the catheter.

An exemplary stylet and method for installing catheters in accordance with the present invention will now be described with reference to the figures, wherein like numbers indicate like parts. FIG. 1A illustrates schematically a coronal cross-section of a mammalian head 90 with a catheter 91 implanted into a brain 95 using a conventional stiff wire stylet 92. The surgeon accesses the brain 95 through a small aperture 93 formed in the skull 94. The stylet 92 is used to push the pliable catheter 91 through the brain tissue 95, until it enters the target ventricle 96.

Figure 1B:
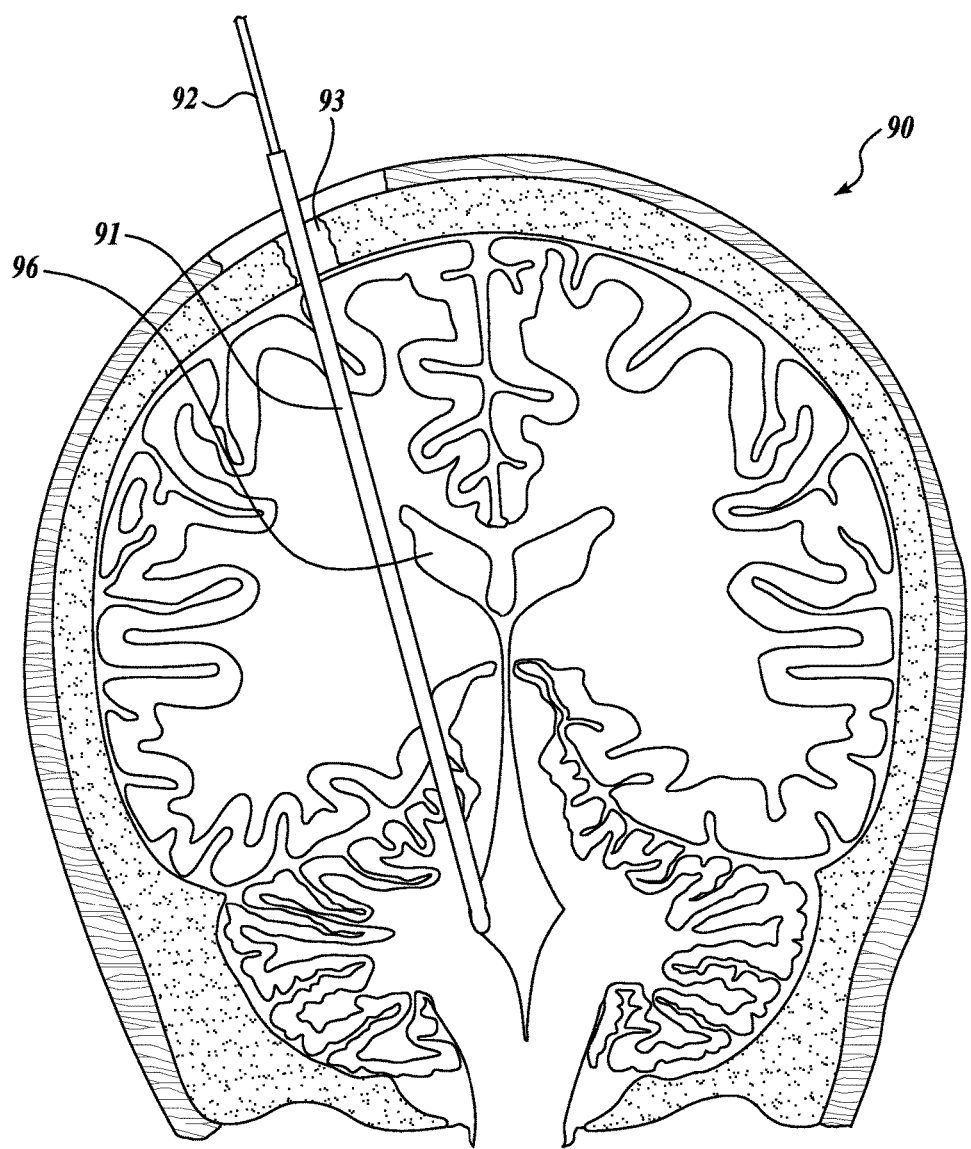

FIG. 1B illustrates schematically the mammalian head 90, wherein the angular positioning of the stylet 92 is slightly off target, resulting in the catheter 91 completely missing the desired target ventricle 96.

As discussed above, it is difficult to align the stylet 92 with the target ventricle 96 based solely on external landmarks. The task is challenging even if an MRI scan or similar image of the brain is available.

A method and stylet in accordance with the present invention is disclosed that uses a non-imaging ultrasonic device or system to aid the surgeon in aligning and guiding the stylet (and catheter) to a desired interior location within an anatomical body. The stylet may be used, for example, to align and guide a catheter toward one of the lateral ventricles 96 in the mammalian brain 95. As used herein, a non-imaging ultrasonic device is defined to be any system or device that uses ultrasound to locate an internal anatomical feature and is not configured to generate an image of the internal anatomical feature. In an exemplary embodiment, a stylet is disclosed having a non-imaging ultrasonic device to aid in guiding a catheter to intersect a target ventricle within the brain.

Ultrasound or ultrasonic waves are pressure waves having a frequency greater than 20 kHz. An ultrasonic wave is typically generated with a transducer, for example, a piezoelectric transducer disposed in a housing. An ultrasound pulser board, or pulser, is typically used to control the operation of the transducer(s) through one or more transmit/receive chips. The pulser controls the timing and frequency of the transducer(s) to generate desired ultrasonic pulses. An ultrasound pulser may have a variety of pre-programmed options for number of pulses in a group, signal frequency, etc. In some ultrasonic devices the ultrasonic waves are generated in a continuous wave mode. However, more typically ultrasonic waves are generated in a pulsed mode wherein wave pulses comprising a relatively small number of waves are generated in spaced packets that are separated in time by periods with no signal generation. An ultrasonic transducer may be operable to both generate ultrasonic waves (i.e., vibrate in response to an applied current) and to detect ultrasonic waves (i.e., generating a current in response to ultrasonic pressure waves). Ultrasonic waves generated by the transducer can be focused directionally into a relatively narrow beam, sometimes referred to as beam forming. Such focusing may be accomplished by the shape of the transducer, with an acoustic lens disposed in front of the transducer, or by a combination of the transducer shape and an acoustic lens. Such ultrasonic beam forming is known in the art, see, for example, U.S. Pat. No. 4,207,901, to Nigam, which is hereby incorporated by reference. See also, U.S. Pat. No. 8,102,734, to Sliwa et al., which is also hereby incorporated by reference.

The transducers can operate in one or both of A-mode and M-mode. Here 'A-mode' refers to a continually updated display of ultrasound defined along a line in time, translated to a line in space through use of an estimate of the speed of sound in tissue, generally approximately 1500 m/s. Here 'M-mode' refers to a sweep of A-mode information, where the A-mode information is given along one axis (that axis representing time, or, distance from the edge of the stylet, for example), and time of measurement given along the other axis. One version of ultrasound relies on the differential backscatter of ultrasound energy from the edges of the target. Another relies on ultrasound to detect and assay the differential motion of the edges of the ventricles relative to surrounding tissue ('tissue pulsatility'). A third relies on ultrasound to detect and assay average blood flow speed and direction towards/away from the direction of the stylet in a given pixel ('color Doppler').

When ultrasonic waves are transmitted through a medium, for example, through tissue, the waves are partially scattered or reflected when they encounter changes in the acoustic impedance of the medium. The acoustic impedance of a medium is defined as the product of its density and acoustic velocity. The magnitude of the scattering will depend in part on the magnitude and abruptness of the change in acoustic impedance. As an ultrasonic wave packet travels through an inhomogeneous medium, for example a mammalian organ, portions of the ultrasonic wave will be reflected or otherwise scattered. Some of the ultrasonic energy will also be attenuated. Reflected and scattered ultrasonic waves can be detected by an ultrasonic transducer that experiences the reflected wave. If the time that an ultrasonic wave was generated, the speed of sound in the medium, and the time a reflected wave was detected are known, then the distance from the transducer to the site of the reflection can be readily calculated. This same information can be used to generate estimates of the spatial and temporal distribution of blood flow speed and/or direction as well as of tissue movement and direction (e.g., tissue pulsatility).

Figure 2:
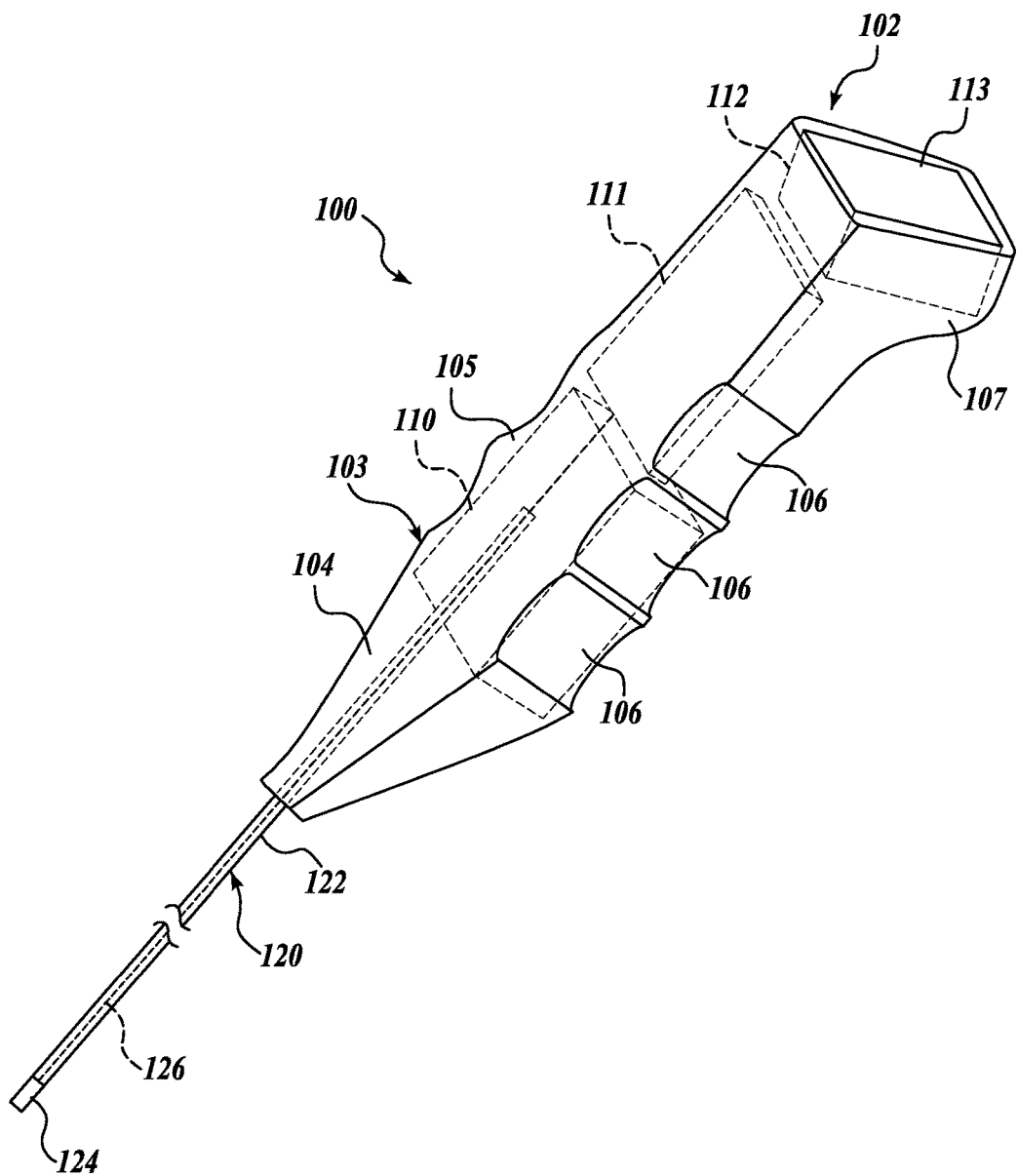
FIG. 2 is a perspective view of a stylet in accordance with the present invention, configured for implanting a catheter into a ventricle.

FIG. 2 illustrates a stylet 100 in accordance with the present invention comprising a handle assembly 102 and a stiff wire assembly 120. The handle assembly 102 includes an outer enclosure 103 with a tapered distal portion 104, an intermediate portion 105 that may optionally be ergonomically designed with grip recesses 106 to facilitate manual control of the handle assembly 102, and an enlarged proximal portion 107. The outer enclosure 103 encloses a power supply 110, a circuit assembly 111, and an indicator display 112. The circuit assembly 111 and indicator display 112 are energized by the power supply 110, and the circuit assembly 111 drives the status of the indicator display 112. The indicator display 112 includes a proximal face 113 that is visible from above the handle assembly 102. In a particular embodiment, the proximal face 113 is directly over and perpendicular to the stiff wire assembly 120.

The stiff wire assembly 120 comprises an elongate tubular member 122 that extends into and is supported by the handle assembly 102. An ultrasonic device 124 is fixed to a distal end of the tubular member 122. In a current embodiment, the ultrasonic device 124 comprises a single ultrasonic transducer, for example, a piezoelectric transducer, that is configured to selectively operate in a transmit mode to generate packets of ultrasonic waves or in a receive mode to detect reflected ultrasonic waves. In another embodiment, the ultrasonic device 124 comprises a small array of transducers, for example, a two-by-two array, a three-by-three array, or the like. Optionally, the ultrasonic device 124 may include one or more acoustic lenses (not shown), as are known in the art, to more narrowly focus the ultrasonic waves. Optionally, a catheter 160 (see FIG. 5) may be provided that includes an acoustic lens 162 at its distal end.

The ultrasonic device 124 is connected to the power supply 110 and to the circuit assembly 111 with a cable 126 that extends through the length of the tubular member 122. The ultrasonic device 124 is powered by the power supply 110 and controlled by the circuit assembly 111. The output from the ultrasonic device 124 is also transmitted to the circuit assembly 111.

While in certain embodiments the elongate member 122 is a stiff wire tubular assembly, it will be apparent to persons of skill in the art that elongate members having various properties may be selected to accommodate a particular task. It is contemplated, for example, that the elongate member may comprise a guide wire, surgical needle, of which many types are known in the art, and curved or curvable elongate members. Flexible elongate members are also contemplated by the present invention. In some applications the elongate member need be only stiff enough to guide a catheter through the tissue.

Figure 3:
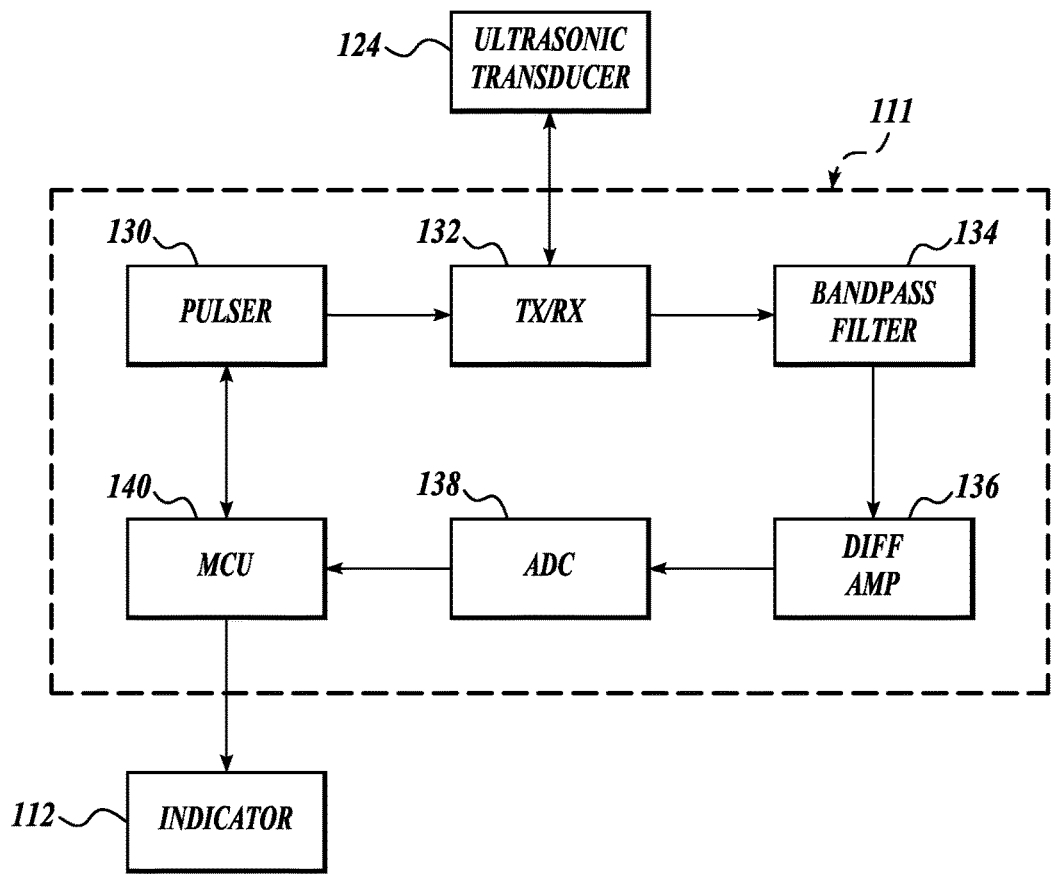
FIG. 3 is a block diagram of the circuit assembly components for the stylet shown in FIG. 2.

FIG. 3 is a block diagram illustrating a currently preferred embodiment of the circuit assembly 111. The circuit assembly 111 includes an ultrasound transmit pulser 130 that provides timing signals to a transmit/receive (Tx/Rx) chip 132 connected to the ultrasonic device 124. The Tx/Rx chip 132 also receives signals from the ultrasonic device 124 representing ultrasonic waves detected by the device 124. The detected signals are processed and digitized through a bandpass filter 134, a differential amplifier 136, and an analog-to-digital converter ("ADC") 138, before being analyzed by a microprocessor 140. In an exemplary embodiment, for convenience, the microprocessor is implemented in a microcontroller unit ("MCU") 140. The MCU 140 analyzes the signal, and determines how to set the indicator display 112 located on the handle assembly 102.

In a current embodiment, the ultrasonic pulser 130 is a Supertex® MD1822DB3 board having a variety of pre-programmed options for driving the ultrasonic device 124. The input voltages to the pulser 130 determine the output voltages. In an initial prototype, the pulser 130 was set to 8 pulse cycles/group, 10 MHz (to match the 10 MHz resonance frequency of the ultrasonic device 124), and output swing voltages of +100 V and −100 V. The Tx/Rx chip 132 accommodates both the ultrasound pulser 130 output and the transducer device 124 response within the same channel and protects the other components by preventing the high voltage output of the pulser 130 from reaching any of the other circuitry except for the ultrasonic device 124. The Tx/Rx chip 132 is configured to allow only voltages below a 2 V threshold from passing through to the remaining circuitry.

The bandpass filter 134 is implemented with an ADA4817 low noise, high gain-bandwidth-product operational amplifier, which allows for high amplification of the 10 MHz ultrasound response signal. A second order bandpass filter design using a single op-amp was selected because it requires fewer chips, decreasing overall costs. The differential amplifier 136 is configured to level shift the signal from a signal centered at 0 V to a signal centered at 1.5 V, which is in the input voltage range for the ADC 138.

The ADC 138 selected is an 8-bit parallel output, 80 MSPS (million samples per second) device, which is configured to satisfactorily meet Nyquist requirements (the Nyquist sampling theorem states that to get a unique representation of the frequency content of a signal, the signal must be sampled at a rate twice the frequency of the highest frequency component of the signal) from a 10 MHz ultrasound signal. The MCU 140 reads the output pins of the ADC 138 and processes the signal to control the status of the indicator 112. The MCU 140 also controls the operation of the pulser 130.

The received reflected or scattered ultrasound signal (sometimes referred to as the "return signal") may be analyzed to determine when the ultrasonic device 124 and, therefore, the stiff wire assembly 120, is aligned with the target ventricle 96. In systems having more than one transducer, the signal may also provide information indicating the direction to rotate the stylet 100 to orient the stiff wire assembly 120 toward the target ventricle.

To use the stylet 100 for inserting an EVD catheter the patient is first prepared conventionally, typically by producing one or more small apertures 93 (see FIG. 1A) through the patient's skull 94. The catheter 91 is placed over the stiff wire assembly 120 of the stylet 100. The surgeon holds the handle assembly 102 and places the distal tip of the stiff wire assembly 120 and catheter 91 adjacent the patient's brain 95, through the aperture 93. The initial placement and orientation of the stylet 100 may be determined in a conventional manner, using external landmarks. The ultrasonic device 124 is energized and the surgeon may look straight down over the top of the handle assembly 102 to view the indicator display 112. The surgeon reorients the stylet 100 by pivoting it about its tip until the indicator display 112 gives information to the surgeon that suggests that the stiff wire assembly 120 is aligned with the target ventricle 96. The surgeon then urges the stylet 100 through the tissue 95 until the catheter enters the target ventricle 96.

In a current embodiment the indicator or proximal face 113 of the indicator 112 is disposed directly over the stiff wire assembly 120 and perpendicular to the axis of the tubular member 122. In this configuration, the surgeon does not need to look away from the stylet 100 and can view the stylet 100 in the direction of insertion. In a particular embodiment, the stylet 100 further comprises a detector, for example, an electrical resistance or pressure gauge, to identify when the tip of the stylet 100 enters the target ventricle 96. The stylet 100 then signals the surgeon when the target ventricle 96 is breached. For example, an audible or visual signal may be generated.

Because the ultrasonic device 124 is a non-imaging ultrasonic device, the transducer(s) may be operated in the one-dimensional mode, sometimes referred to as A-mode or amplitude mode. The brain is a non-homogeneous organ, and ultrasonic waves will scatter and reflect from various structures within the brain. For example, three different sources of information in the return signal may be used singly or in combination to locate the target ventricle as discussed below.

The fluid-filled ventricle has different acoustic impedance than the surrounding brain tissues. An ultrasonic wave that encounters a ventricle will therefore partially scatter or reflect due to the abrupt change in acoustic impedance. A non-reflected portion of the ultrasonic wave will also transit through the ventricle and will partially reflect when it encounters brain tissue on the opposite side of the ventricle. This double-reflection of the ultrasonic wave produces a characteristic return signal to the ultrasonic device 124 that can be used to identify a return signal from the target ventricle 96.

In addition, the brain tissue is perfused with blood through the capillary system in the brain, which results in a detectable expansion and contraction of the brain with each heart beat due to the difference between the systolic and diastolic blood pressures. Each ventricle, however, is filled with CSF liquid. The walls that define the edges of the ventricle move relatively more than other regions of the brain. Moreover, as the ventricle expands and contracts, opposing walls move in generally opposite directions. The return signals received by the ultrasonic device 124 may be analyzed using Doppler techniques to identify this motion. In particular, the return signals may be filtered using a low-pass filter to more readily detect this low-frequency component in the return signal and aid in identifying the ventricle.

A third signal that may be used to identify the ventricle is due to the continuous blood flow through the brain tissue, which produces a high frequency component within each ultrasound signal that represents the average blood flow speed and direction within that signal. This is the basis of color Doppler analysis. When used most often, color Doppler analysis is used to highlight bulk flow within major blood vessels such as arteries or veins. When turned away from such major blood vessels and aimed primarily at organs of the body perfused via secondary arteries/veins as well as capillaries, the result is, typically, signal-by-signal variations in blood flow speed and direction. This information is often represented within diagnostic ultrasound machines as a variation in shades of red and blue. We refer to this kind of signal as "sparkle" in the detected signal, though to be clear it is based on any variation in color Doppler analysis. However, blood does not flow through the ventricles. Cerebral spinal fluid does move within ventricles, but in bulk flow on spatial scales much larger than blood within the brain. Therefore, the return signal received by the ultrasonic device 124 may be analyzed to identify and measure the "sparkle" component in the signal. In particular, the return signals may be filtered using a high-pass filter to more readily detect this higher-frequency component in the return signal, to aid in identifying the ventricle, which will have reduced sparkle relative to the surrounding tissue.

Figure 4:
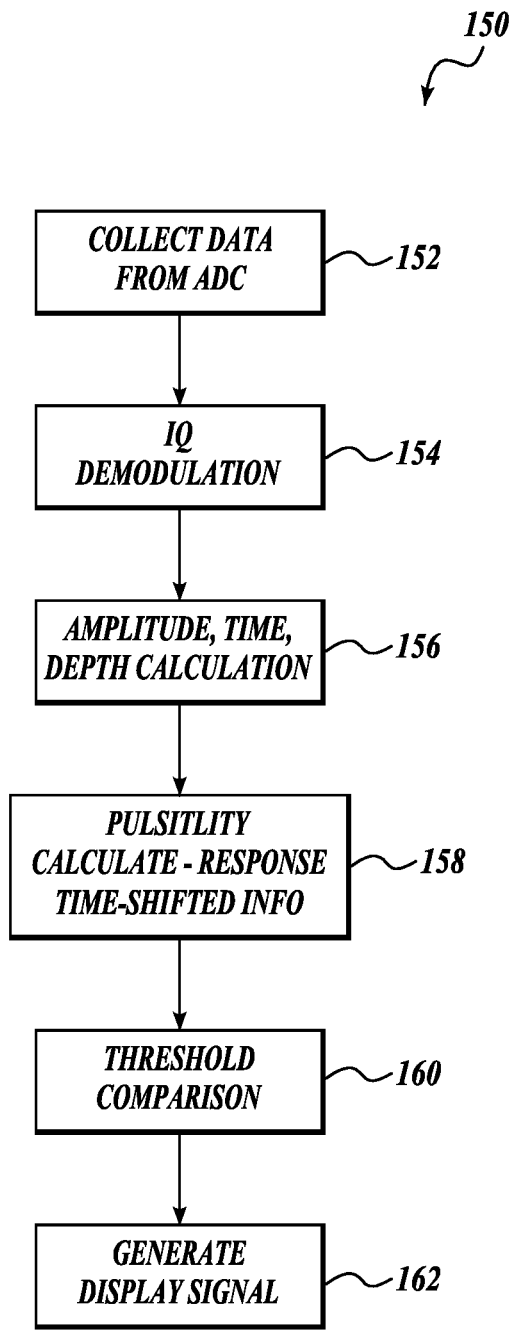
FIG. 4 is flow chart illustrating a method for operating the stylet shown in FIG. 2.

An exemplary method 150 for processing the received ultrasound signals is illustrated in FIG. 4. The MCU 140 receives data 152 from the ADC 138 representing the scattered ultrasound signals detected by the ultrasonic device 124. To reduce the amount of data without losing essential information, a complex base-band modulation technique with bandwidth reduction is used. In particular, IQ demodulation 154 (in-phase/quadrature-phase demodulation), removes frequencies from the signal other than the fundamental frequency of the transducer(s). The IQ demodulation 154 includes down-mixing, wherein the real valued signal is multiplied with a complex sinusoid signal, low-pass filtering to remove the negative frequency spectrum and noise outside the desired bandwidth, and decimation, reducing the sampling frequency without losing information from the signal. The IQ demodulation 154 preserves the information content in the band-pass signal, and the original signal can be reconstructed from the IQ-signal, as is known in the art.

Amplitude, time, and/or depth calculations 156 use the timing information determined from the detected signal. For example, the timing characteristics (e.g., the difference between the time the ultrasonic pulse was generated and the time of a detected response) may be used to estimate the distance from the ultrasonic device 124 and the source of the reflection. A predetermined distance range may establish thresholds for reflected signals that could indicate alignment with the ventricle. If a target tissue has a thickness, for example a ventricle, a reflection signal may be detected from an ultrasonic pulse first engaging the target tissue, and again as the now attenuated signal leaves the target tissue. The resulting pair of reflection signals may be used to estimate the thickness of the target.

A pulsatility calculation 158 analyzes the time characteristics of the reflected signal, i.e., the shape of the signal over time, to determine if the signal indicates a moving boundary or two moving boundaries that would indicate ventricular motion related to normal periodic changes in the blood pressure.

A threshold comparison 160 may be used to interpret the amplitude and pulsatility results to determine if they are consistent with expected values for a ventricle. Based on the results of the threshold comparison 160, a signal is generated 162 to control the status of the indicator display 112. For example, the indicator 112 or portions of the proximal face 113 may flash to indicate the desired alignment is achieved. Alternatively, the face 113 may be set to display the calculated distance to the target ventricle and/or a direction to rotate the stylet 100 to better align with the ventricle.

Because the stylet 100 does not rely on imaging the patient, instead, comprising one or a relatively small number of transducers in the ultrasonic device 124, the stylet 100 can be made relatively inexpensively. In a current embodiment, the stylet is designed and configured to be a single-use disposable device.

Figure 5:
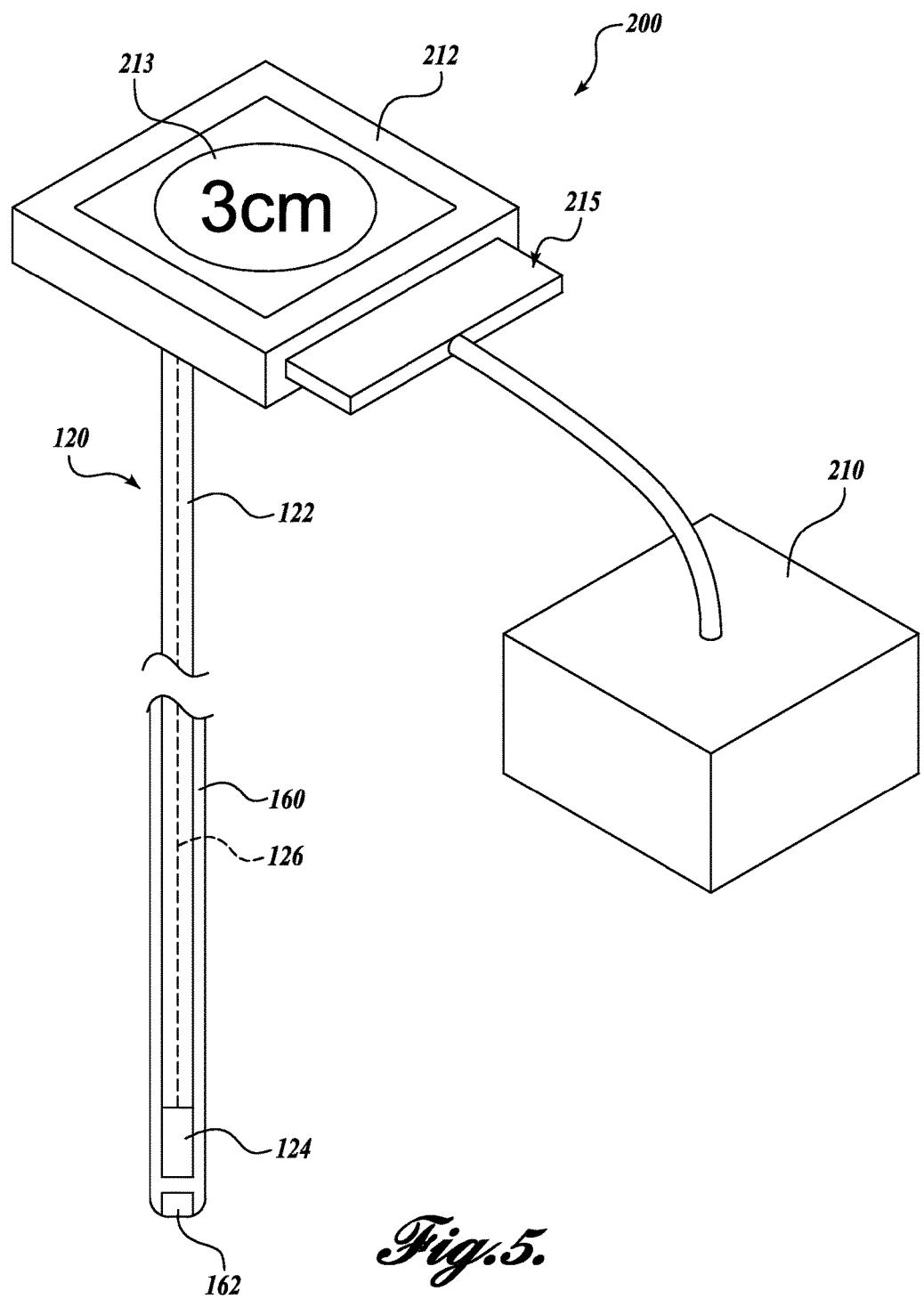
FIG. 5 illustrates a second embodiment of a stylet in accordance with the present invention wherein a control system is provided separate from the stylet.

FIG. 5 illustrates an alternative configuration in accordance with the present invention wherein a stylet 200 is similar to the stylet 100 described above, except that certain of the components described above are not integrated into the stylet 200. These components are provided in an external control device 210. In this embodiment, a stylet 200 includes the elongate stiff wire assembly 120 having the ultrasonic device 124 attached at a distal end. The ultrasonic device 124 is connected to an indicator display 212 fixed to the stiff wire assembly 120. A proximal face 213 is preferably disposed directly over, and perpendicular to the stiff wire assembly 120. In the illustrated embodiment, the proximal face 213 indicates the calculated distance to the detected ventricle. A removable cable assembly 215 connects the stylet 200 with the external control device 210. The control device 210 includes one or more of the power supply 110, circuit assembly 111, pulser 130, Tx/Rx chip 132, bandpass filter 134, differential amplifier 136, ADC 138, and MCU 140, substantially as described above. In this embodiment, the stylet 200 is disposable, and the external control device 210 is reusable.

In FIG. 5, a catheter 160 is illustrated and is slidably disposed on the elongate tubular member 122. The catheter 160 is a relatively flexible device. In some embodiments, a catheter may have an open distal end sometimes called a "fish mouth catheter." In FIG. 5, the distal end of the catheter 160 is closed with an acoustic lens 162.

As discussed above, the non-imaging ultrasonic device 124 may comprise a single ultrasonic transducer or may comprise a small plurality of transducers. For example, the ultrasonic device may comprise four transducers arranged in a two-by-two array, five transducers disposed in a cruciform pattern, or nine transducers arranged in a three-by-three array. Other arrangements are also contemplated. It will be appreciated that the ultrasonic device 124 is disposed on the distal end of the stylet tubular member 122, and therefore, the array of transducers must be sufficiently small.

Figure 6:
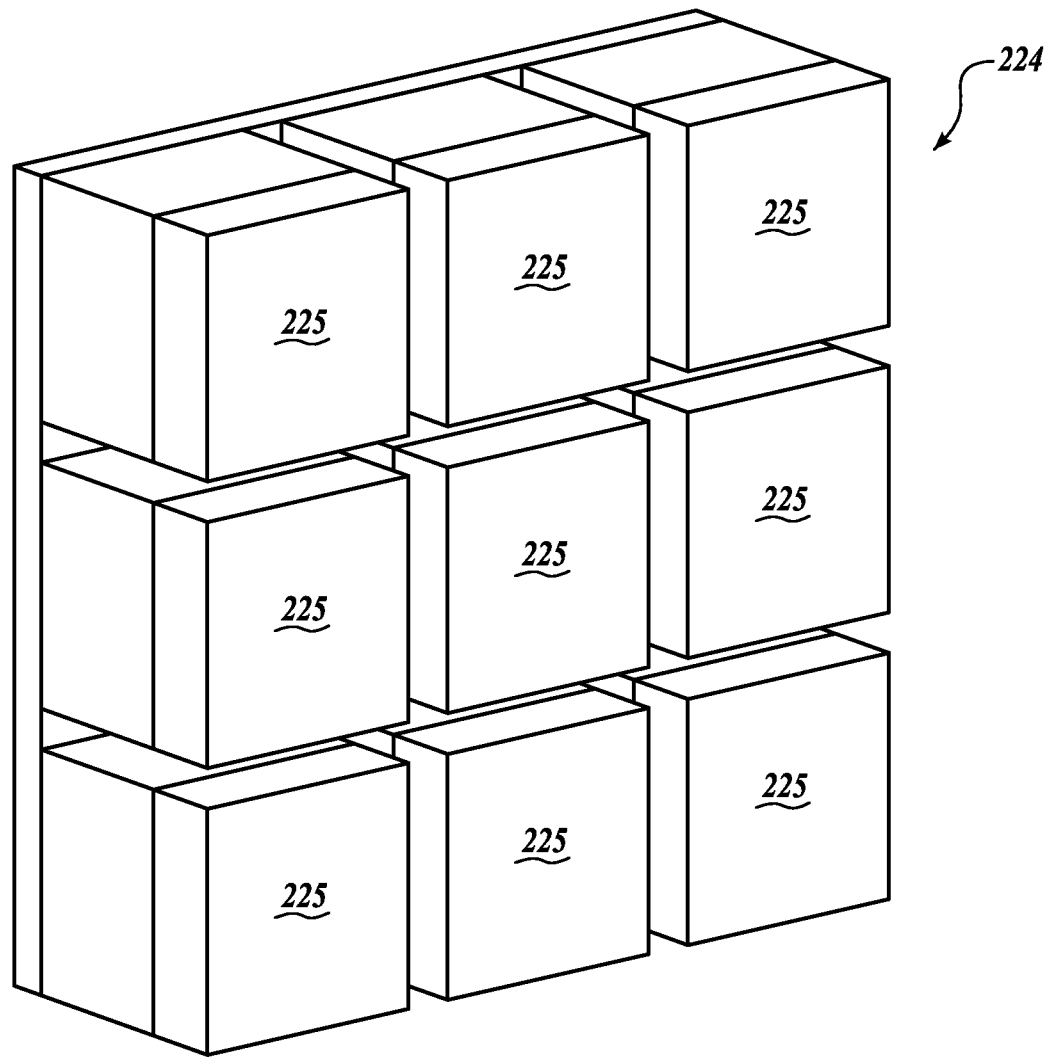
FIG. 6 illustrates a multi-transducer embodiment of the ultrasonic device for the stylet shown in FIG. 2.

A currently preferred embodiment of a multi-transducer ultrasonic device 224 is shown in FIG. 6 and comprises a three-by-three element square array of transducer elements 225. In this embodiment, each transducer element 225 is configured to selectively generate ultrasound, thereby maximizing the power and directivity of the diagnostic ultrasound. Each of the transducer elements 225 is also operable to detect or receive ultrasound.

In this exemplary embodiment, the multi-transducer device 224 measures approximately 1 mm square and comprises nine separate transducer elements 225 formed from a single crystal. The elements 225 are oriented in a common direction and are coplanar. When all nine elements are energized simultaneously, the array sends out a highly directional beam of ultrasound. In receive mode, the active elements comprise six of the elements 225 in a crossing or cruciform pattern.

When the stylet 100 is not well aligned with the target structure, for example, the target ventricle, ultrasound energy returning from the target will return at an angle with respect to the face of the device 224. Elements 225 nearest to the target will detect the reflected energy earlier than elements 225 disposed farther from the target. Therefore, difference in the arrival time of the detected signal can be analyzed to determine the direction that the stylet 100 should be rotated to align with the target ventricle. The MCU 140 may be configured to analyze the return signals and provide feedback to the surgeon through the indicator display 112 to facilitate proper alignment of the stylet 100.

For example, in one embodiment the proximal face 113 (FIG. 2) of the indicator display 112 is configured with a plurality of individually controllable indicators, for example, light-emitting diodes, that can be controlled by the MCU 140 to selectively illuminate to indicate a direction to pivot the stylet 100. In another example, a "level bubble-type" indicator is provided on the proximal face 113 such that the bubble indicator is centered on the proximal face 113 when the stylet 100 is properly aligned.

It should be appreciated that the elements 225 may be controlled in different patterns without departing from the present invention. For example, the corner elements 225 may be operated only in transmit mode, and the remaining elements 225 may be operated only in receive mode. Other possible arrangements will be apparent to persons of skill in the art.

Although an exemplary system is disclosed that is configured to aid the surgeon in aligning the stylet 100 with an internal tissue-fluid boundary in the brain, i.e., a ventricle, and may be used to facilitate implanting a catheter 160, it will be apparent to persons of skill in the art that the present invention may readily be applied to aligning other instruments or devices with internal tissue-fluid boundaries in a body. For example, it is frequently desirable to locate and penetrate an internal tissue-fluid boundary with a needle. As discussed in U.S. Pat. No. 8,282,565, to Mahapatra et al., which is hereby incorporated by reference, common medical needle types include a Barker Spinal needle, a Tuohy needle, a Tuohy-Flowers needle, a Hustead needle, a Weiss needle, a Special Sprotte needle, and a Crawford needle. Such needles are sometimes inserted into a patient with a stylet that extends through the needle lumen, and provides the benefit of preventing tissue from entering the needle lumen. A non-imaging ultrasonic stylet such as the stylet 100 described above, may be used to aid the surgeon in aligning the needle with a desired tissue-fluid boundary. For example, the stylet 100 may aid in aligning a needle with the epidural space of a patient.

The specific exemplary embodiment described above is intended to illustrate a typical and currently preferred embodiment of the circuit assembly 111, and it will be readily apparent to persons of skill in the art that there are a number of changes that can be made to this specific embodiment without departing from the present invention.

The invention claimed is:

1. A stylet for use in medical procedures, comprising:
   an elongate member comprising a stiff wire tubular assembly configured to receive a catheter and configured for placing the catheter into a tissue;
   an indicator configured to selectively activate a first status prompt to indicate a desired alignment of the elongate member;
   wherein the stiff wire tubular assembly further comprises a non-imaging ultrasonic device fixed to a distal end of the elongate member, and further wherein the non-imaging ultrasonic device is configured to selectively generate ultrasonic waves in a direction longitudinally aligned with the elongate member, and to detect scattered ultrasonic waves;
   a microprocessor operably connected to the non-imaging ultrasonic device and configured to control the selective generation of ultrasonic waves, and to process the detected scattered ultrasonic waves to detect an internal tissue-fluid boundary;
   wherein the microprocessor is operably connected to the indicator, and the microprocessor causes the indicator to activate the first status prompt when the internal tissue-fluid boundary is detected, indicating the elongate member is aligned with the detected internal tissue-fluid boundary, prior to placing the catheter into the tissue.

2. The stylet of claim 1, wherein the indicator is attached to a proximal end of the elongate member.

3. The stylet of claim 1, wherein the indicator is configured to selectively activate a second status prompt indicating a non-desired alignment of the elongate member.

4. The stylet of claim 3, wherein the second status prompt includes a marking to indicate a direction to pivot the stylet toward the desired alignment.

5. The stylet of claim 1, wherein the first status prompt also indicates a distance to the internal tissue-fluid boundary.

6. The stylet of claim 1, wherein the elongate member comprises a rigid elongate member, a flexible elongate member, a guidewire, a cannula, a needle, a curved elongate member, or a straight elongate member.

7. The stylet of claim 1, wherein the non-imaging ultrasonic device comprises a single ultrasonic transducer that is configured to selectively operate in a transmit mode, wherein the ultrasonic transducer generates ultrasonic waves, and in a receive mode, wherein the ultrasonic transducer detects ultrasonic waves.

8. The stylet of claim 1, wherein the ultrasonic device comprises a plurality of ultrasonic transducers comprising fewer than ten transducers.

9. The stylet of claim 8, wherein the plurality of ultrasonic transducers are disposed in an array wherein, a distal face of all of the transducers are coplanar.

10. The stylet of claim 8, wherein the plurality of ultrasonic transducers are formed from a single crystal.

11. The stylet of claim 1, further comprising a pulser, a transmit/receive chip, a bandpass filter, and an analog-to-digital converter mounted with the microprocessor to form a circuit assembly that is operable to control the operation of the ultrasonic device and to analyze the detected ultrasonic waves.

12. The stylet of claim 11, further comprising a cable that extends from the ultrasonic device, through the elongate member, and to the circuit assembly to operably connect the ultrasonic device with the circuit assembly.

13. The stylet of claim 11, further comprising a handle formed as an enclosure that houses the indicator and fixedly attaches to the elongate member.

14. The stylet of claim 13, wherein the handle encloses the circuit assembly and further comprises a power supply operably connected to the circuit assembly.

15. The stylet of claim 1, further comprising an external control unit that houses the microprocessor and further comprises a pulser, a transmit/receive chip, a bandpass filter, and an analog-to-digital converter mounted with the microprocessor to form a circuit assembly that is operable to control the operation of the ultrasonic device and to analyze the detected ultrasonic waves, wherein the circuit assembly is operably and releasably connected to the indicator and to the ultrasonic device.

16. The stylet of claim 1, further comprising an elongate catheter configured to slidably receive the elongate member and the ultrasonic device.

17. The stylet of claim 16, wherein the catheter further has a distal end that is either open or is closed with an acoustic lens.

18. The stylet of claim 1, wherein the indicator is disposed directly over a proximal end of the elongate member and is oriented perpendicular to the elongate member.

19. The stylet of claim 1, wherein the indicator comprises a display that is configured to selectively display the first status prompt.

20. The stylet of claim 1, wherein the indicator comprises a display that is configured to selectively indicate the thickness of the internal tissue-fluid boundary.

21. The stylet of claim 1, wherein the indicator is configured to selectively generate an audible prompt to indicate the desired alignment.

22. The stylet of claim 1, wherein the indicator is configured to selectively generate a haptic prompt to indicate the desired alignment.

23. The stylet of claim 1, wherein the microprocessor and the indicator are in wireless communication.

* * * * *